(12) United States Patent
Nielsen et al.

(10) Patent No.: US 7,507,870 B2
(45) Date of Patent: Mar. 24, 2009

(54) WOUND DRESSING

(75) Inventors: John Stern Nielsen, Allerod (DK);
Mette Irene Kolte, Soborg (DK); Borge Gundersen, Tikob (DK)

(73) Assignee: Coloplast A/S, Humlebaek (DK)

( * ) Notice: Subject to any disclaimer, the term of this patent is extended or adjusted under 35 U.S.C. 154(b) by 229 days.

(21) Appl. No.: 10/495,433

(22) PCT Filed: Nov. 18, 2002

(86) PCT No.: PCT/DK02/00772

§ 371 (c)(1),
(2), (4) Date: Nov. 19, 2004

(87) PCT Pub. No.: WO03/043553

PCT Pub. Date: May 30, 2003

(65) Prior Publication Data

US 2005/0080372 A1 Apr. 14, 2005

(30) Foreign Application Priority Data

Nov. 23, 2001 (DK) .............................. 2001 01752

(51) Int. Cl.
*A61F 13/00* (2006.01)
(52) U.S. Cl. .................. 602/58; 602/42; 602/48; 602/55
(58) Field of Classification Search ............ 602/41–59; 128/888–890; 424/443–449; 604/304–308
See application file for complete search history.

(56) References Cited

U.S. PATENT DOCUMENTS

| 3,419,006 | A |  | 12/1968 | King |  |
| 3,645,835 | A |  | 2/1972 | Hodgson |  |
| 3,972,328 | A |  | 8/1976 | Chen |  |
| 4,367,732 | A |  | 1/1983 | Poulsen et al. |  |
| 4,538,603 | A |  | 9/1985 | Pawelchak et al. |  |
| 4,552,138 | A |  | 11/1985 | Hofeditz et al. |  |
| 4,867,748 | A |  | 9/1989 | Samuelsen |  |
| 5,015,228 | A | * | 5/1991 | Columbus et al. | 604/513 |
| 5,051,259 | A |  | 9/1991 | Olsen et al. |  |
| 5,086,764 | A | * | 2/1992 | Gilman | 602/42 |
| 5,533,962 | A |  | 7/1996 | Peterman et al. |  |
| 5,540,922 | A | * | 7/1996 | Fabo | 424/402 |
| 5,641,506 | A |  | 6/1997 | Talke et al. |  |
| 5,643,187 | A |  | 7/1997 | Naestoft et al. |  |
| 5,714,225 | A |  | 2/1998 | Hansen et al. |  |
| 5,728,071 | A | * | 3/1998 | Watson et al. | 604/180 |
| 5,998,692 | A | * | 12/1999 | Gilding | 602/41 |

(Continued)

FOREIGN PATENT DOCUMENTS

| DK | 127 578 B | 3/1979 |
| DK | 148 408 B | 7/1985 |
| DK | 154 747 B | 12/1988 |
| DK | 154 806 B | 12/1988 |
| EP | 0 097 846 | 1/1984 |

(Continued)

*Primary Examiner*—Kim M Lewis
(74) *Attorney, Agent, or Firm*—Jacobson Holman PLLC

(57) ABSTRACT

A wound dressing including a backing layer, an adhesive layer and an absorbent layer between the backing layer and the adhesive layer, in which the adhesive layer secures the absorbent layer to the backing layer and the adhesive layer is interrupted in at least one zone exposing at least a part of the skin contacting surface of the absorbent layer. At least the skin-facing surface of the adhesive layer is provided with a non-detachable, non-adhesive cover layer.

19 Claims, 1 Drawing Sheet

U.S. PATENT DOCUMENTS

| | | | |
|---|---|---|---|
| 6,011,194 A | 1/2000 | Buglino et al. | |
| 6,191,335 B1 * | 2/2001 | Robinson | 602/41 |
| 6,242,665 B1 | 6/2001 | Malowaniec | |
| 6,379,695 B1 | 4/2002 | Donati et al. | |
| 6,440,513 B1 | 8/2002 | Kiebele et al. | |
| 6,566,575 B1 * | 5/2003 | Stickels et al. | 602/41 |
| 6,700,033 B1 | 3/2004 | Marcussen et al. | |
| 7,154,017 B2 * | 12/2006 | Sigurjonsson et al. | 602/41 |
| 2003/0088202 A1 * | 5/2003 | Gilman | 602/46 |
| 2003/0153860 A1 * | 8/2003 | Nielsen et al. | 602/43 |

FOREIGN PATENT DOCUMENTS

| | | |
|---|---|---|
| EP | 0 272 149 | 6/1988 |
| EP | 0 352 086 | 1/1990 |
| EP | 0 415 183 | 3/1991 |
| GB | 1 280 631 | 7/1972 |
| GB | 1 586 182 | 3/1981 |
| HU | 220313 | 11/1999 |
| HU | 0000445 | 10/2000 |
| HU | 0000045 | 1/2001 |
| HU | 0003347 | 2/2001 |
| HU | 223450 | 3/2001 |
| HU | 0104466 | 3/2002 |
| SE | 365 410 | 3/1974 |
| WO | 88/06894 | 9/1988 |
| WO | 98/31402 | 7/1998 |
| WO | 99/06077 | 2/1999 |
| WO | WO 99/07349 | 2/1999 |
| WO | 01/37888 | 5/2001 |

* cited by examiner

WOUND DRESSING

This is a nationalization of PCT/DK02/00772 filed Nov. 18, 2002 and published in English.

FIELD OF THE INVENTION

The invention relates to a wound dressing, especially a non-adherent wound dressing being suitable for handling exuding wounds.

BACKGROUND OF THE INVENTION

Wound dressings with layers for absorbing body fluids are known in the art. Absorbent layers are provided for the uptake of body fluids, especially wound exudate, so as to enable the wound dressing to keep a constant moist environment over the wound site, and at the same time avoiding maceration of the skin surrounding the wound.

Much effort has been directed to enhancing the rate of uptake and capacity of the wound dressing, in particular the absorbent layer, to uptake body fluids. Absorbent layers in wound dressings have comprised hydrocolloid, super absorbents, foams and synthetic materials which have extensive capacity to absorb body fluids, especially wound exudate.

However, increasing the capacity and rate of fluid uptake within a wound dressing may give rise to problems, both in assuring that the body fluids do not migrate from the wound dressing and in assuring the wound does not dry out.

Hydrocolloid dressings are some of the most efficient and mostly used dressings, being skin-friendly, absorbent and capable of creating moist wound healing conditions. However, when used on some exuding wounds, the absorption rate tends to be too low. The advantages of the hydrocolloid dressing are the ability of creating a moist wound healing environment and acting as a barrier against bacteria.

A frequent problem when treating exuding wounds is maceration. Usually the absorbent part of the dressing is optimised to substantially vertical absorption, so that the skin surrounding the wound is not exposed to the exudate in order to avoid maceration of this healthy, but fragile skin. However, these properties are s limiting the absorption capacity of the dressing to the part of absorbent material being directly over the wound. Barrier cream/skin conditioning paste, such as zinc paste, may be used on the surrounding skin in order to avoid the maceration, but the paste will often inhibit both the adhesive tack of the dressing as well as the ability of absorbing exudate.

Highly exuding wounds are often treated with foams or alginates, which are capable of absorbing high amounts of exudate but requires additional cover dressings, as well as the risk of maceration is high. The retention of foam is low, which may be a problem when used on body parts being exposed to pressure.

A way of overcoming the problems with limited absorption capacity is to create a dressing with high permeability. This is usually done by using a backing layer being more permeable to vapour, but still liquid and bacteria impermeable. Using such a film the absorption capacity will rise when the permeability rises, enhancing the absorption capacity of the dressing. The capacity rises due to evaporation of moisture through the backing layer.

The skin surrounding leg ulcers is often very fragile and thus easily damaged. Wound dressings comprising a direct contact between pressure sensitive adhesives, such as hydrocolloid adhesives or medical acrylate based adhesives, which are often used on commercially available film products, and the skin are not suitable for treatment of such wounds. Traumatic removal of the adhesive dressings with damage to the skin is common, and suggest the use of non-adhesive products.

The skin may be so damaged that exudate trickles from the skin surrounding the wound, being a challenge to most of the well-known dressings. Furthermore, the area of the lower limb may comprise special demands to the flexibility properties of the dressing due to the anatomical complexity of the area combined with the movability of the joints of the ankle and malleolus.

Another important consideration in the treatment of leg ulcers is that the dressing must not give rise to pressure sores. A non-adhesive dressing is usually combined with compression therapy. Thus, a dressing being flat, soft and without sharp edges is preferred.

It is often necessary to treat the fragile skin with ointments or pastes in order to neutralise the impact of the pressure sensitive adhesive on the skin, increasing the risk of leakage on products solely based on pressure sensitive adhesives, as the absorption of the exudate is dramatically reduced when the skin and thus the adhesive area is covered with a lipid containing layer, such as a zinc paste or silicone-products.

Leg ulcers are known to be highly exuding, and may give rise to increased risk of leakage and maceration, if the used wound dressing does not have a sufficient capacity of exudate handling with respect to time and amount. Hydrocolloid products as the above mentioned will often be unsuitable for use in wound healing stages with medium to high exudate level, especially if the skin is covered with a lipid containing products.

International Patent Application No. WO A 98/31402 discloses a wound dressing comprising a perforated wound contacting layer such as a film or a net, a backing layer, and between these two layers is a fibrous absorbent layer. The absorbent layer and the backing layer are combined by heat-lamination. This bandage is absorbent and highly permeable, but may give rise to maceration as the absorbent part may be in contact with the surrounding skin. Leakage may also be a problem.

In International Patent Application No. WO 99/06077 is disclosed a non-adhesive wound dressing which is in the form of an island dressing. The dressing comprises a top film, coated with an adhesive, an absorbent pad of a size smaller than the top layer mounted on the adhesive layer, in order to create an adhesive-covered flange around the absorbent pad, and a non woven layer covering all of the skin contacting surface of the dressing. The permeability of the dressing may however be limited due to the overall adhesive coating as well as maceration may occur along the edges of the absorbent pad, extending further than the wound.

In wound dressings comprising multiple layers including highly permeable films, the different layers of the dressing are often combined by the use of adhesive, usually by coating the backing layer, fully or partly, with adhesive, in order to hold the components of the dressing together. The adhesive coating will however, decrease the permeability of the film significantly.

Alternatively, the dressing may be produced by combining the layers of the dressing by lamination. However, the heat and pressure of the lamination process may change the permeability properties of the backing layer, as well as the structure of the absorbent layer may be crushed.

Furthermore, if the layers of the dressing are joined by lamination solely, the edge zone of the dressing may have very little if any absorbent properties, increasing the risk of maceration and leakage of the surrounding skin.

The flexibility of a dressing wherein the layers are tied together by adhesive or lamination may also be reduced. This may give rise to handling problems and leakage when used on curved body parts.

Thus, there is still a need for a non-adhesive flexible, highly absorbent wound dressing being capable of absorbing large amounts of wound exudate without giving rise to maceration.

BRIEF DESCRIPTION OF THE INVENTION

The present invention relates to a wound dressing comprising a backing layer, an adhesive layer and an absorbent layer between the backing layer and the adhesive layer.

BRIEF DESCRIPTION OF THE DRAWINGS

The invention is explained more in detail with reference to the drawings in which.

DETAILED DESCRIPTION OF THE INVENTION

Figure 1:
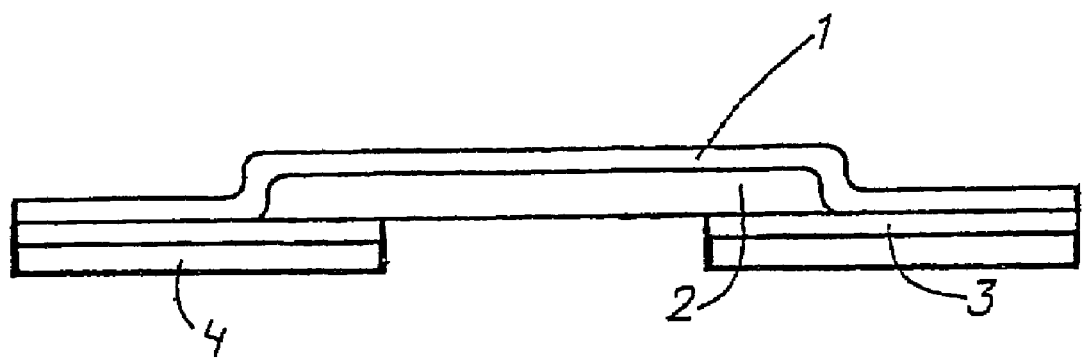
FIG. 1 shows a cross-section of an embodiment of the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention relates to a wound dressing comprising a backing layer, an adhesive layer and an absorbent layer between the backing layer and the adhesive layer, wherein the adhesive layer secures the absorbent layer to the backing layer and the adhesive layer is interrupted in at least one zone exposing at least a part of the skin contacting surface of the absorbent layer. At least the skin-facing surface of the adhesive layer is provided with a non-detachable, non-adhesive cover layer.

A dressing according to the invention is thus in the form of a single unit, not an assembly. The dressing will provide a high initial absorption due to the direct contact between the wound and the absorbent layer, and a high absorption capacity due to the lack of adhesive or lamination between the backing layer and the absorbent layer combined with a high permeability of the backing layer. A dressing in a single unit decrease the risk of leakage compared to an assembled or re-openable dressing.

The adhesive will serve as a sealant of the parts of the dressing, but more important, the adhesive decrease the risk of maceration, as any moisture, e.g. in the form of exudate or sweat will be absorbed by the adhesive and thus protecting the surrounding skin from maceration from the wound. The cover layer will not interfere with this function of the adhesive as the cover layer will be permeable to exudate and moisture.

The dressing according to the invention is especially suitable for use on body parts having special demands to the flexibility of the dressing such as the lower limb, where the anatomical complexity of the area around the joints and malleolus often is difficult to apply a dressing to.

A non-adhesive dressing according to the invention is usually combined with compression therapy. The dressing may also be secured to the patient by use of tape or wraps.

The cover layer, preferably comprising a soft and pliable material, combined with the other layers of the dressing provides a soft and flexible dressing, which feels pleasant against the skin. The backing layer and the cover layer may be combined along the edge portion by the adhesive layer, providing a thin, flexible and non-adhesive flange around the absorbent layer of the dressing. This flange may be capable of adapting to the contours of the treated body part as well as following the movements of the body part. The fragile skin is protected by the non-adhesive cover layer, and the adhesive layer between the cover layer and the backing layer may absorb any exudate or perspiration and thus protect the skin against maceration.

In a preferred embodiment of the invention the backing layer and the absorbent layer are "mutually displaceable", by which is meant, capable of displacement with respect to one another such that there is free movement of the backing layer relative to the absorbent layer.

By locating the backing layer and the absorbent layer adjacent to each other and mutually displaceable, an enhanced flexibility and permeability is obtained. The flexibility is enhanced due to the higher bending and twisting flexibility, as well as when the absorbent layer absorbs exudate and thereby expands, the free movement of the backing layer will allow more space over the expanding region of the absorbent layer and thus a larger surface for evaporation.

If the backing layer is coated, fully or partly with adhesive, the permeability of the backing layer will decrease. When lamination is used instead, the influence of heat and/or pressure may disrupt the permeability qualities of the backing layer, as well as the absorber, which often is a fragile matrix structure, may be damaged.

Maximum permeability of the backing layer is obtained when no adhesive is applied between the backing layer and the absorbent layer. By avoiding, or diminishing the use of adhesive or lamination, a maximum permeability of moisture from the absorbent layer to the environment is achieved.

In one embodiment of the invention all of the non-skin-facing surface of the absorbent layer is adjacent to the backing layer.

The adhesive layer may extend over a part of the surface between the absorbent layer and the backing layer.

The backing layer and the absorbent layer may have connection points or lines. The points or lines may be achieved by dots or lines of adhesive or they may be created by welding. It is preferred that the points or lines are arranged in such a way that at least a part of the backing layer and the absorbent layer are still mutually displaceable.

The adhesive layer may cover at least a fraction of the skin-facing surface of the absorbent layer. The adhesive layer may fully cover the skin-facing surface of the absorbent layer or the layer may be coated in a pattern or with one or more apertures or slits.

The adhesive layer may preferably comprise an aperture in the area covering the absorbent layer. The aperture may especially be located centrally over the wound and will render it possible to have a fast absorption as the absorbent layer will be in direct contact with the exudate, as the exudate will not have to pass through the adhesive layer first.

The apertures may be in the form of a pattern of smaller or larger apertures. Preferably the apertures are in the area of the adhesive layer under the absorbent layer.

Preferably the aperture has about the same dimensions as of the wound. This will enhance the absorption rate over the wound, while the fragile skin next to the wound will be protected by the adhesive layer.

The aperture in the adhesive layer may be enlarged to adapt to the size of the wound. The enlargement may be done by scissors or by the use of pre-cuts lines in the cover layer and the adhesive layer, enabling easy removal of excess layer before application. The pre-cuts lines may e.g. be in the form of concentric circles, squares, or a helix.

The adhesive layer may comprise a reinforcing layer. The reinforcing layer may be in the form of a web or a net, or a non woven, fibres, etc. The reinforcing layer may ease the handling during application and removal as well as the strength of the dressing is enhanced. When the absorbent layer absorbs exudate the adhesive layer will be wetted not only from the skin-facing side but also from the top side, by absorbed exudate from the absorbent layer. This may alter the strength properties of the adhesive layer, and demand for a strengthening layer.

The skin-facing adhesive surface of the dressing may be provided with a non-detachable, non-adhesive cover layer.

Preferably, the cover layer may be permeable to aqueous fluids.

In one embodiment of the invention the cover layer may be in the form of a woven or non-woven, knits, a perforated film or laminate or a foam.

The woven may be in the form of a polymer net or a cotton or gauze.

The perforated polymer film may be a polyurethane film.

The foam may be any suitable foam, such as a polyurethane foam.

Preferably, the cover layer is in the form of a non-woven.

In a preferred embodiment of the invention the cover layer is a non-woven, more preferred a non-woven based upon polyethylene terephthalate (PET) fibres, and most preferred PET fibres with polytetrafluoroethylene (PTFE) on the skin-contacting surface.

In another embodiment of the invention the cover layer may be in the form of a coating of the adhesive skin-facing surface with a powder or a paste, such as zinc oxide or talc or zinc paste.

In a third embodiment of the Invention the cover layer may be in the form of a cohesive layer, such as an adhesive without adhesive tack, an elastomer or a hydrogel.

In one embodiment of the invention the cover layer is capable of absorbing aqueous liquids such as perspiration and wound exudate.

When applying a non-adhesive dressing to a body part it is often difficult to hold the dressing in place over the wound while applying the fixation means, such as wraps or bandages. A third hand would be appreciated in the process, e.g. when securing a non-adhesive wound dressing to difficult areas such as curved body parts, e.g. the leg, and fastening it with a bandage with the use of only two hands. Usually this may be difficult, as one hand is needed to hold the dressing in place while another two hands are needed to control the bandage strip and wrap it around the wound dressing and body part.

A way of achieving a third hand may be to provide the skin-contacting surface of the dressing with adherent or high friction properties. Such a dressing may be slightly adhesive or adherent, enough for holding the dressing in place until properly secured by a bandage or the like, but not adhesive enough to give rise to the well-known problems of adhesive dressings. The dressing will still need a secondary dressing or bandage to secure it properly to the treated body part.

These adherent or high friction properties may be achieved in different ways. In one embodiment of the invention the cover layer is provided with one or more perforations. Through these perforations the adhesive surface is exposed, providing discrete adhesive locations on the skin-facing surface of the dressing. These locations render it possible to adhere the dressing to the wound site while securing the dressing properly by applying the fixation means.

The adhesive locations may be of any suitable number and size, and arranged in patterns or arrays or randomly spread over the skin-facing surface. It is preferred that the adhesive locations are situated at the portion of the cover layer being furthest away from the wound, thus minimizing any undesired effect the adhesive to the fragile skin surrounding the wound. When the dressing is changed, it would be unlikely if the adhesive locations of the new dressing would be placed at exactly same location as the old one, thus the skin will rarely be exposed to the adhesive more than once.

In another embodiment of the invention the third hand may also be achieved by using a cover layer having an open structure exposing the adhesive through the pores of this open structure. Only a negligible amount of adhesive will be exposed through the pores of the cover layer, but enough to provide the dressing with low adherent properties.

In yet another embodiment of the invention dots or lines of adhesive or adherent material may be placed on the skin-facing surface of the cover layer. The adhesive may be printed on the cover layer or be in the form of a layer of a randomised or systematic pattern. The adhesive markings may preferably comprise a pattern or a framing along the edge of the dressing.

Even though the term "adhesive" is used in the foregoing it is understood that the term may cover any substance having adherent properties, such as adhesives, silicone or rubbery substances, petrolatum or the like, as the adhesive of the third hand only serves to immobilise the dressing until it is properly fastened by a secondary bandage. This function may also be achieved by using a material with high friction properties. Any substance, being skin-friendly and able to adhere or have the required friction for the purpose, may be suitable for use in this invention.

If the dressing of the invention is provided with a skin-contacting surface having adhesive or adherent properties, the skin-contacting surface may preferably be covered by a release-liner, which may be removed before use.

The cohesive layer may have absorbent properties, e.g. comprise hydrocolloid particles.

The cover layer may in one embodiment of the invention cover all of the skin-facing surface of the dressing.

In a preferred embodiment of the invention the cover layer may cover the adhesive part of the skin-facing surface of the dressing. In this embodiment of the invention the cover layer thus comprises any aperture in the adhesive layer.

In one embodiment of the invention the surface of the cover layer may be slightly smaller than the adhesive surface, leaving an adhesive flange along the outer rim of the dressing.

In an embodiment of the invention the cover layer is substantially non-absorbent.

It is preferred that the cover layer is capable of transporting liquid. This renders it possible for the moisture to diffuse from the skin surface through the cover layer to the adhesive, leaving the skin-contacting surface substantially dry.

The absorbent layer may comprise an exudate distributing material. To have full benefit of the absorbent material in the absorbent layer a liquid distributing layer, acting as a wick, may be incorporated in the dressing. The wicking layer renders it possible to utilise the areas of absorbent layer not being located right above the wound as well as the wetted surface of the absorbent layer will be enlarged and thus the evaporation through the backing layer will be enhanced.

The absorbent layer may be in the form of one or more layers, e.g. a multilayer, comprising layers of different absorption properties in order to optimise the absorption capacity of the absorbent layer.

The absorbent layer may be in the form of a matrix structure, e.g. with incorporated particles.

When the absorbent layer comprises a material capable of distributing the absorbed exudate, full utilisation of the absorption capacity in the dressing may be obtained.

The absorbent layer may comprise any absorbent material known per se being suitable for use in wound care devices, e.g. polyacrylate, CMC, cellulose or derivatives thereof, gums, foam or alginate.

A material being capable of retaining and/or distributing the liquid is preferred.

The absorbent layer may comprise super absorbent particles (SAP) and/or super absorbent fibres (SAF).

The absorbent layer may comprise a horizontally spreading/absorbent layer.

The feature of horizontal absorption and/or spreading of exudate is contrary to normal practice in absorbent wound dressings, as the perception of a good dressing is vertical absorption in order to avoid the skin surrounding the wound being exposed to the exudate. In the dressing of the present invention horizontal spreading is not a problem because the surrounding skin is protected by the adhesive layer.

In one embodiment of the invention the absorbent layer may comprise spheres or inclusions of absorbent material, in a structure like pearls on a string. Between the pearls a material capable of distributing the wound exudate is located.

The absorbent layer may comprise a stop layer on the skin-facing surface for preventing any speck or fluff from the absorbent layer to enter the wound. The stop layer may be of any suitable material known in the art being capable of retaining absorbent material, such as a cellulose tissue, non-woven or a perforated polymeric film, knits, PP, PE, polyester or lycra.

The absorbent layer may further comprise a wound contacting layer at the wound-facing surface. This wound contacting layer may prevent adherence to the wound as well as in growth of the dressing. The layer may preferably be highly permeable to wound exudate. Preferably, the wound contacting layer is in the form of a polymer net.

The absorbent layer may be embossed or pre-cut in order to enhance flexibility of the dressing.

The backing layer may be liquid impervious but vapour permeable or it may be of a type having a higher water permeability when in contact with liquid water than when not in contact. The backing layer may be of any suitable material known per se for use in the preparation of wound dressings e.g. a foam, a nonwoven or a polyurethane, polyethylene, polyester or polyamide film.

A suitable material for use as a backing layer is a polyurethane. A preferred low friction film material is disclosed in U.S. Pat. No. 5,643,187.

It is preferred that the adhesive has absorbent properties. The adhesive may absorb exudate leaking from the central part of the dressing, as well as it may absorb perspiration and exudate excreted from the surrounding skin. The moisture diffuses through the cover layer and into the adhesive layer, leaving the skin contacting cover layer dry against the skin, decreasing the risk of maceration.

The adhesive layer of the invention may be any skin-friendly adhesive known per se, e.g. an adhesive comprising hydrocolloids or other moisture absorbing constituents for prolonging the time of use. The adhesive may suitably be of the type disclosed in GB patent specification No. 1 280 631, in DK patent specifications Nos. 127,578, 148,408, 154,806, 147,226 and 154,747, in EP published application Nos. 0 097 846 and 0 415 183, in SE published application No. 365,410, in WO publication No. 88/06894, in U.S. Pat. No. 4,867,748, and in NO published application No. 157,686. Especially preferred are the adhesives disclosed in U.S. Pat. Nos. 4,367,732 and 5,051,259 and DK patent specification No. 169,711.

In a preferred embodiment of the invention the adhesive comprises a hydrocolloid adhesive. The use of a hydrocolloid adhesive may provide an excellent protection of the surrounding skin of the wound by inducing the moist wound healing environment, and yet avoiding maceration. The hydrocolloids capability of absorbing moisture renders it possible to absorb any leaking exudate from the dressing or from the surrounding skin.

Furthermore, when exudate is spread in the absorbent layer it leads to wetting of the adhesive layer from the side opposite the skin. The hydrocolloid will absorb any moisture trying to enter the surface of the skin surrounding the wound, and thus decrease the risk of maceration.

The adhesive layer may also comprise any other adhesives, chosen from a wide range of different types of adhesives for instance the acrylic types, and types derived from PIB, polyurethanes, EVA-compounds, APAO's, silicones, polyvinyl ether etc.

In one embodiment of the invention the adhesive surface of the dressing may be provided with a detachable cover layer in the form of a permeable, non-adhesive layer. The cover layer may be removed like a release-liner if an adhesive dressing is desired, and stay on the dressing in the case of a non-adhesive dressing is desired. The detachable cover layer may be pre-cut into multiple parts, such as concentric circles or squares, rendering it possible to remove the desired part of the cover layer in order to expose a part of the adhesive.

The dressing according to the invention may comprise one or more active ingredients.

The wound dressing according to the invention may comprise one or more active ingredients, e.g. a pharmaceutical medicament. This opens for a combined medical treatment of a wound, where the dressing absorbs wound exudate and the pharmaceutical medicaments will be applied to the wound. The pharmaceutical medicaments or active ingredients will either be incorporated in the wound dressing or migrate to the wound surface and promote its function.

Examples of such pharmaceutical medicaments includes a cytochine such as a growth hormone or a polypeptide growth factor such as TGF, FGF, PDGF, EGF, IGF-1, IGF-2, colony stimulating factor, transforming growth factor, nerve stimulating growth factor and the like giving rise to the incorporation of such active substances in a form being apt to local application in a wound in which the medicament may exercise its effect on the wound, other medicaments such as bacteriostatic or bactericidal compounds, e.g. iodine, iodopovidone complexes, chloramine, chlorhexidine, silver salts such as sulphadiazine, silver nitrate, silver acetate, silver lactate, silver sulphate, silver sodium thiosulphate or silver chloride, zinc or salts thereof, metronidazol, sulpha drugs, and penicillin's, tissue-healing enhancing agents, e.g. RGD tripeptides and the like, proteins, amino acids such as taurine, vitamins such ascorbic acid, enzymes for cleansing of wounds, e.g. pepsin, trypsin and the like, proteinase inhibitors or metalloproteinase inhibitors such as Illostat or ethylene diamine tetraacetic acid, cytotoxic agents and proliferation inhibitors for use in for example surgical insertion of the product in cancer tissue and/or other therapeutic agents which optionally may be used for topical application, pain relieving agents such as lidocaine or chinchocaine, emollients, retinoids or agents having a cooling effect which is also considered an aspect of the invention.

The active ingredient may also comprise odour controlling or odour reducing material such as charcoal.

The active ingredient may be present in the dressing, but not in direct contact with the wound, or it may migrate to the wound when exposed to wound exudate.

The cover layer may be impregnated with zinc-paste or other skin-conditioning or healing enhancing materials.

The adhesive layer may together with the cover layer be capable of adsorption or absorption and retention of high molecular parts of the wound exudate, e.g. proteins. The handling may be in the form of a mechanical collection of wound exudate in e.g. a three-dimensional non-woven, a loosely knitted or woven material, a fleece material, a material with a wavy surface, or a filament material like a rya, or it may be chemically, by binding the high molecular parts of the wound exudate, or it may be enzymatically by degrading the high molecular parts of the wound exudate.

The absorbent layer may be softened by incorporation of glycerine.

DETAILED DESCRIPTION OF THE DRAWINGS

In FIG. 1 is shown one embodiment of the invention. The dressing comprises a backing layer (1) adjacent to an absorbent layer (2) and an adhesive layer (3) covering at least a part of the skin-facing surface of the dressing. A part of the skin-facing surface of the absorbent layer is left without the adhesive layer in order to facilitate rapid uptake of exudate from the wound. The skin-facing surface of the adhesive layer is provided with a cover layer (4) of the same proportions as the adhesive layer, leaving the skin-contacting surface of the dressing non-adhesive.

Figure 2:
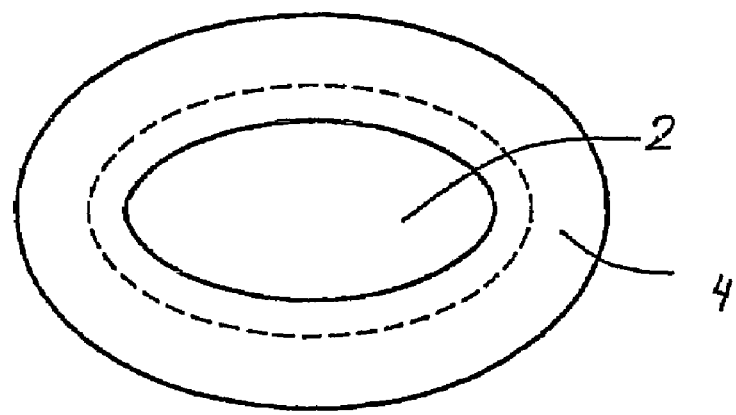
FIG. 2 shows a top view of another embodiment of the invention.

FIG. 2 shows another embodiment of the invention shown from above, with the skin-facing surface up. The cover layer (4) is located at the skin-facing surface of the adhesive layer and extends over the edge portion of the absorbent layer (2), having substantially the same dimensions as the backing layer of the dressing. The centre of the adhesive layer defines an aperture under the absorbent layer. The size of the aperture may be enlarged, e.g. by cutting with a pair of scissors, in order to costumize the size of the aperture to the size of the wound. An intermediate layer of approximately the same size of the absorbent layer may be located between the adhesive layer and the absorbent layer. The intermediate layer prevents the adhesive from adhering to the absorbent layer rendering removal of excess adhesive layer without damaging the absorbent layer possible. This intermediate layer may be any suitable material such as a non-woven, a permeable film or a foam.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A wound dressing comprising a backing layer, an adhesive layer and an absorbent layer between the backing layer and the adhesive layer, said adhesive layer securing the absorbent layer to the backing layer and said adhesive layer being interrupted in at least one zone, exposing at least a part of the absorbent layer as a skin-contacting surface, and an adhesive skin-facing surface of the adhesive layer being provided with a non-detachable, non-adhesive cover layer such that a skin-contacting surface of said wound dressing is substantially non-adhesive in use, said backing layer and said absorbent layer being mutually displaceable such that said backing layer is free to move relative to said absorbent layer.

2. The dressing according to claim 1 wherein the cover layer is in the form of a woven or non-woven, a knit, a perforated film or laminate or a foam.

3. The dressing according to claim 1 wherein the cover layer is in the form of a cohesive layer.

4. The dressing according to claim 1 wherein the cover layer is in the form of a coating of the adhesive skin-facing surface with a powder or a paste.

5. The dressing according to claim 4 wherein said powder or paste is selected from the group consisting of zinc oxide, talc and zinc paste.

6. The dressing according to claim 1 wherein the interrupted zone of said adhesive layer includes an aperture in an area covering the absorbent layer.

7. The dressing according to claim 1 wherein the skin-contacting surface of the dressing is provided with adherent or high friction properties.

8. The dressing according to claim 1 wherein the cover layer covers all of the adhesive skin-facing surface of the adhesive layer.

9. The dressing according to claim 1 wherein the adhesive comprises a hydrocolloid adhesive.

10. The dressing according to claim 1 wherein the dressing includes one or more active ingredients.

11. A wound dressing comprising a backing layer, an adhesive layer and an absorbent layer between the backing layer and the adhesive layer, said adhesive layer having a skin-facing surface and securing the absorbent layer to the backing layer, said adhesive layer also having at least one zone therein in which a part of the absorbent layer is exposed as a skin-contacting surface, and a non-detachable, non-adhesive cover layer provided on said skin-facing surface of the adhesive layer such that a skin-contacting surface of said wound dressing is substantially non-adhesive in use, said backing layer and said absorbent layer being mutually displaceable such that said backing layer is free to move relative to said absorbent layer.

12. The dressing according to claim 11 wherein the cover layer is in the form of a woven or non-woven, a knit, a perforated film or laminate or a foam.

13. The dressing according to claim 11 wherein the cover layer is in the form of a cohesive layer.

14. The dressing according to claim 11 wherein the cover layer is in the form of a coating of the adhesive skin-facing surface with a powder or a paste.

15. The dressing according to claim 11 wherein the zone in said adhesive layer is an aperture in an area covering the absorbent layer.

16. The dressing according to claim 11 wherein the skin-contacting surface of the dressing is provided with adherent or high friction properties.

17. The dressing according to claim 11 wherein the adhesive includes a hydrocolloid adhesive.

18. The dressing according to claim 1 wherein the dressing comprises one or more active ingredients.

19. A wound dressing comprising a backing layer, an adhesive layer and an absorbent layer between the backing layer and the adhesive layer, said adhesive layer securing the absorbent layer to the backing layer and having at least one zone therein in which a part of the absorbent layer is exposed as a skin-contacting surface, and a non-detachable, non-adhesive cover layer provided on a skin-facing surface of the adhesive layer such that a skin-contacting surface of said wound dressing is substantially non-adhesive in use, said skin-contacting surface of said dressing being provided with adherent or high-friction properties to assist in temporarily holding the dressing in place while it is being applied and until it is secured by a bandage or other fastening component.

* * * * *